(12) United States Patent
Fujita

(10) Patent No.: US 9,566,262 B2
(45) Date of Patent: Feb. 14, 2017

(54) ITCH SUPPRESSION BY FUCOXANTHIN

(71) Applicants: THE RITSUMEIKAN TRUST, Kyoto-shi, Kyoto (JP); LOGIC CO., LTD., Uji-shi, Kyoto (JP)

(72) Inventor: Takashi Fujita, Kusatsu (JP)

(73) Assignees: The Ritsumeikan Trust, Kyoto (JP); Logic Co., Ltd., Uji (JP)

( * ) Notice: Subject to any disclaimer, the term of this patent is extended or adjusted under 35 U.S.C. 154(b) by 0 days.

(21) Appl. No.: 15/133,903

(22) Filed: Apr. 20, 2016

(65) Prior Publication Data
US 2016/0310460 A1 Oct. 27, 2016

(30) Foreign Application Priority Data

Apr. 21, 2015 (JP) .................................. 2015-087090

(51) Int. Cl.
| A61K 31/335 | (2006.01) |
| A61K 31/07 | (2006.01) |
| A61K 36/02 | (2006.01) |
| A61K 31/336 | (2006.01) |
| A61K 9/00 | (2006.01) |
| A61K 36/05 | (2006.01) |

(52) U.S. Cl.
CPC ........... *A61K 31/336* (2013.01); *A61K 9/0014* (2013.01); *A61K 36/05* (2013.01)

(58) Field of Classification Search
CPC ....... A61K 31/335; A61K 31/59; A61K 8/975
USPC .............................. 514/475, 725; 424/195.17
See application file for complete search history.

(56) References Cited

U.S. PATENT DOCUMENTS

| 8,454,970 B2 * | 6/2013 | Li ........................ A61K 31/355 424/195.17 |
| 8,834,855 B2 * | 9/2014 | Johnsen ................... A61K 8/33 424/59 |
| 8,871,217 B2 * | 10/2014 | Li ........................ A61K 31/336 424/195.17 |
| 9,199,952 B2 * | 12/2015 | Uekita ...................... A23L 1/30 |

FOREIGN PATENT DOCUMENTS

| JP | 2009-108022 A | 5/2009 |
| JP | 2012-254959 A | 12/2012 |

OTHER PUBLICATIONS

D'Orazio et al., "Fucoxanthin: A Treasure from the Sea," Marine Drugs, 10: 604-616 (2012).
Fujita, "Cosmetech 2014," Presentation by Molecular Toxicology Laboratory, Department of Pharmacy, Ritsumeikan University (Oct. 21, 2014).
Fujita, "Fucoxanthin: Utility for Skin Damage and Atopic Dermatitis," Poster by Molecular Toxicology Laboratory, Department of Pharmacy, Ritsumeikan University (Oct. 21, 2014).
Mio et al., "Fucoxanthin to the Damaged Skin," Presentation by Molecular Toxicology Laboratory, Department of Pharmacy, Ritsumeikan University (Feb. 23, 2015).

* cited by examiner

*Primary Examiner* — Raymond Henley, III
(74) *Attorney, Agent, or Firm* — Leydig, Voit & Mayer, Ltd.

(57) ABSTRACT

The present invention provides a method of suppressing mast cell differentiation and/or itch in the skin of a subject, comprising topically administering to the skin in need thereof an effective amount of fucoxanthin or a derivative thereof.

14 Claims, 8 Drawing Sheets
(7 of 8 Drawing Sheet(s) Filed in Color)

Figure 6
A
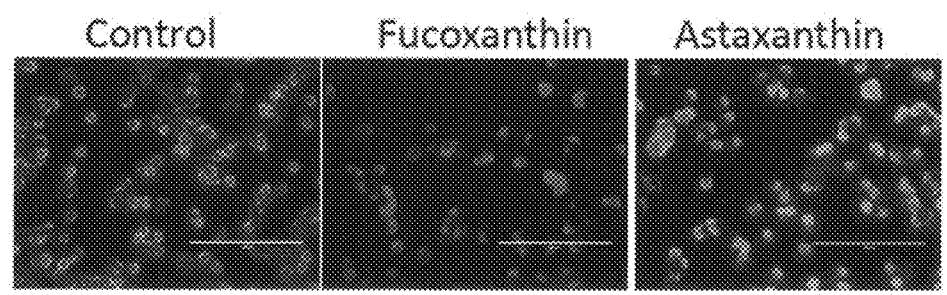
B
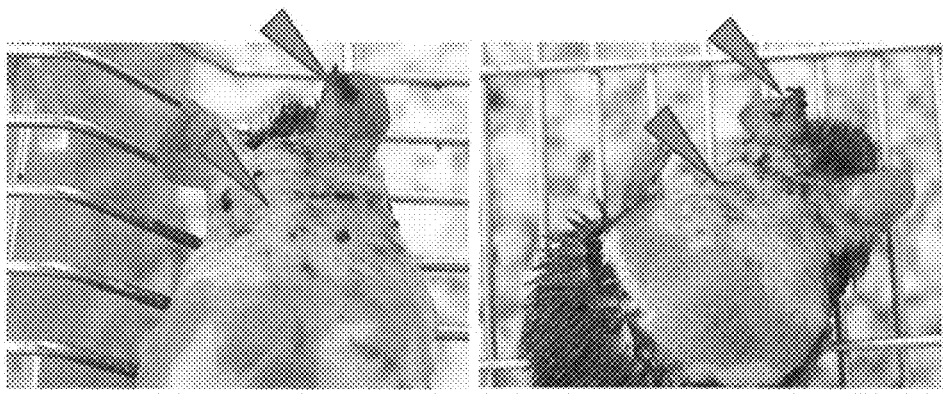

Figure 9
A
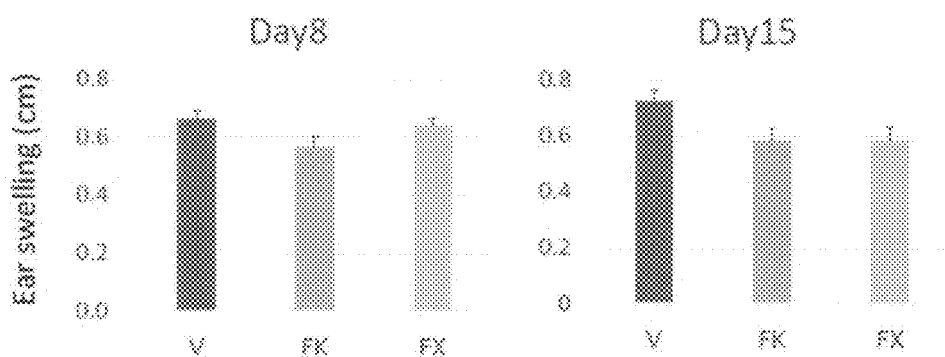
B
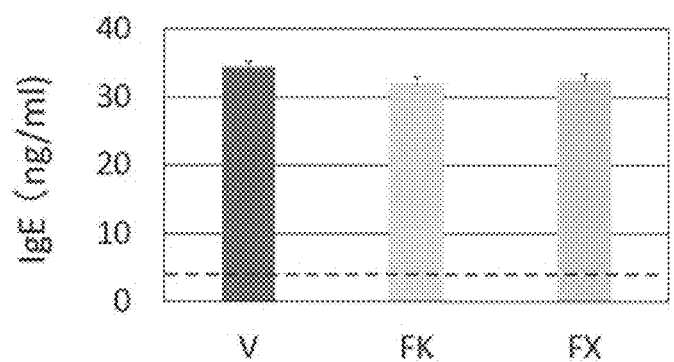

Figure 10
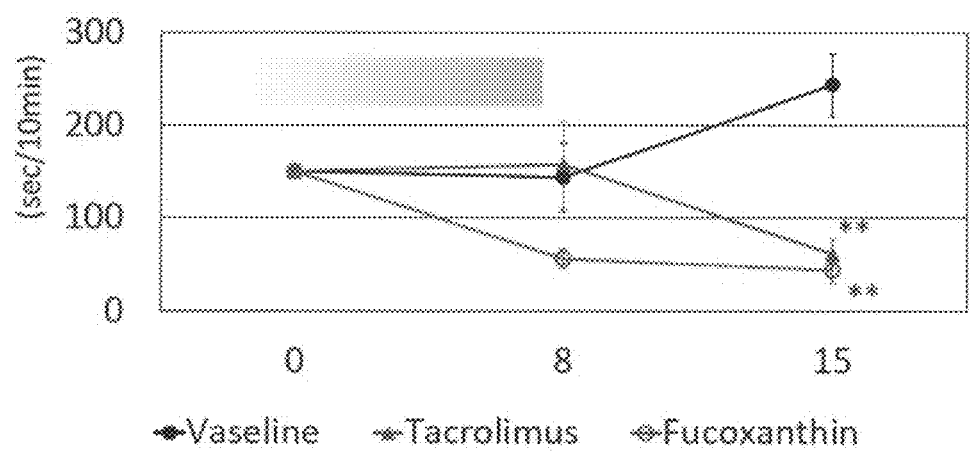
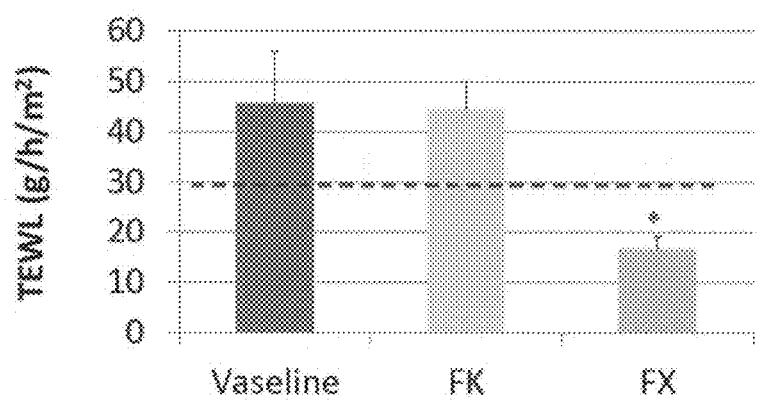

ITCH SUPPRESSION BY FUCOXANTHIN

CROSS-REFERENCES TO RELATED APPLICATION

This application claims the benefit of priority to Japanese Patent Application No. 2015-87090, filed on Apr. 21, 2015, the contents of which are incorporated herein by reference.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 3,427 bytes ASCII (Text) file named "724024Sequence Listing.txt" created Apr. 17, 2016.

TECHNICAL FIELD OF THE INVENTION

The present invention relates to an agent for suppressing mast cell differentiation, in particular, an agent for suppressing itch, comprising a fucoxanthin or a derivative thereof, or a salt thereof.

BACKGROUND OF THE INVENTION

Atopic dermatitis is a kind of hypersensitivity associated with dermal inflammation such as eczema, among the diseases related to an allergic reaction. It is associated with physiological abnormalities including skin dryness and barrier dysfunction caused by stratum corneum abnormality. Various non-specific irritation responses and specific allergic reactions are involved in the development of atopic dermatitis.

Atopic dermatitis is considered to occur by complicated interactions of genetic predisposition, exposure to environment and immunological mechanisms. Due to uncertain pathogenic mechanism, the treatment of atopic dermatitis is limited to application of anti-inflammatory topical medicaments such as corticosteroids and calcineurin inhibitors. However, these compounds cannot completely suppress the onset of atopic dermatitis. No satisfying therapy of atopic dermatitis has been established.

Mast cells are known to cause type I allergic reaction via IgE to mediate many diseases such as atopic dermatitis. Therefore, it is expected that suppression of the function of mast cells enables the treatment of these diseases. The mast cells are known to produce many inflammatory mediators, and be activated by various stimuli to degranulate, thereby releasing such inflammatory mediators. For example, mast cells contain various chemical mediators including histamine. When mast cells recognize an antigen, said recognition triggers activation of membrane enzymes on the mast cells, resulting in the release of granules containing histamine and tryptase. In addition, activation of the cell membrane enzymes increases production and metabolism of arachidonate (arachidonate cascade) and releases its metabolites, leukotriene, platelet activating factor (PAF), prostaglandin thromboxane A2 and the like, from the cell membrane.

Meanwhile, a kind of carotenoids, fucoxanthin, has been considered to act as a provitamin A in a living body and is known to have an antioxidant action suppressing the production of reactive oxygen species (ROS) by oxidation stress in cultured dermal cells. In addition, Kawashima (JP 2012-254959 A) teaches that fucoxanthin suppresses IL-17 production and Th-17 cell differentiation and proposes use of food and drink or an oral drug comprising fucoxanthin or a derivative thereof for the prophylaxis or improvement of Th-17 diseases. Yamada (JP 2009-108022 A) discloses that oral intake of fucoxanthin results in an anti-allergic effect.

However, when fucoxanthin is orally ingested, it is metabolized via liver and mostly functions as a vitamin A-like substance. Vitamin A improves barrier function of mucosal epithelial cells, and degrades and detoxifies lipoperoxides. Since one of vitamins A, retinoic acid, also has a suppressive action against Th-17 cell differentiation, it is strongly suggested that the effects of oral intake of fucoxanthin described in the above-mentioned patent documents are based on its provitamin A activity, namely the active ingredients are its metabolites, vitamin A-like substances.

Yamada (supra) also evaluates the anti-allergic effect of fucoxanthin by using a decrease of serum eosinophils as an index, but it fails to disclose local effects (in particular, itch suppression effect) of fucoxanthin on the skin of hives or atopic dermatitis. Yamada also fails to teach or suggest effects of fucoxanthin on mast cells.

SUMMARY OF THE INVENTION

It is an object of the present invention to provide a novel use of fucoxanthin for drugs, quasi-drugs or cosmetics based on mechanisms of action other than provitamin A activity (as an active ingredient). It is another object of the present invention to provide a novel means for treating dermal diseases associated with itch such as atopic dermatitis.

The present invention is at least in part based on the finding that external application of fucoxanthin or a derivative thereof can remarkably suppress scratching behavior in dermatitis model mice. Also, the present invention is at least in part based on the finding that external application of fucoxanthin can suppress not only degranulation reaction of mast cells but also differentiation into mature mast cells.

Accordingly, the present invention is as follows.

[1] An agent for topical administration for suppressing mast cell differentiation, comprising fucoxanthin or a derivative thereof.

[2] The agent according to [1] above, which is used externally for skin.

[3] The agent according to [1] or [2] above, which is used for suppressing itch.

[4] A method of suppressing mast cell differentiation in the skin of a subject, comprising topically administering to the skin in need thereof an effective amount of fucoxanthin or a derivative thereof.

[5] A method of suppressing itch in the skin of a subject, comprising topically administering to the skin in need thereof an effective amount of fucoxanthin or a derivative thereof.

According to the present invention, various body surface diseases mediated by mast cells can be treated by external application of a drug. In particular, symptoms of dermal diseases, especially itch, can be reduced. Therefore, the present invention can remove the burden of internal use. In addition, the inventive agent is cost-effective since it can be used in a low dose.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 6 shows differences in the effects on BMMCs and NC/Nga mice between fucoxanthin and astaxanthin. Fucoxanthin suppressed granule formation in BMMCs (A) and ameliorated clinical symptom of dermatitis in NC/Nga mice (B), whereas astaxanthin did not show such in vitro and in vivo effects.

FIG. 9 shows that neither fucoxanthin nor tacrolimus affects ear swelling and serum IgE level in NC/Nga mice. (A) The lengths of the auricular lymph nodes in Vaseline-treated (V), fucoxanthin-treated (FX) and tacrolimus-treated (FK) Nc/Nga mice at 5 weeks after starting treatment with respective compounds. (B) Serum IgE concentrations in Vaseline-treated (V), fucoxanthin-treated (FX) and tacrolimus-treated (FK) Nc/Nga mice at 5 weeks after starting treatment with respective compounds. The dashed line indicates the upper limit of normal range.

FIG. 10 shows that fucoxanthin is faster-acting than tacrolimus on itch in NC/Nga mice. (A) Time spent for scratching behavior (sec/10 minutes) in Vaseline-treated (filled circle), fucoxanthin-treated (open circle) or tacrolimus-treated (filled triangle) NC/Nga mice at 5 weeks after starting treatment with respective compounds. **: $p<0.01$ vs Vaseline-treated mice. (B) Transdermal water loss (TEWL) in the skin of Vaseline-treated, fucoxanthin-treated (FX) or tacrolimus-treated (FK) NC/Nga mice at 5 weeks after starting treatment with respective compounds. *: $p<0.05$. The dashed line indicates the upper limit of normal range.

DETAILED DESCRIPTION OF THE PREFERRED EMBODIMENTS

Figure 1:
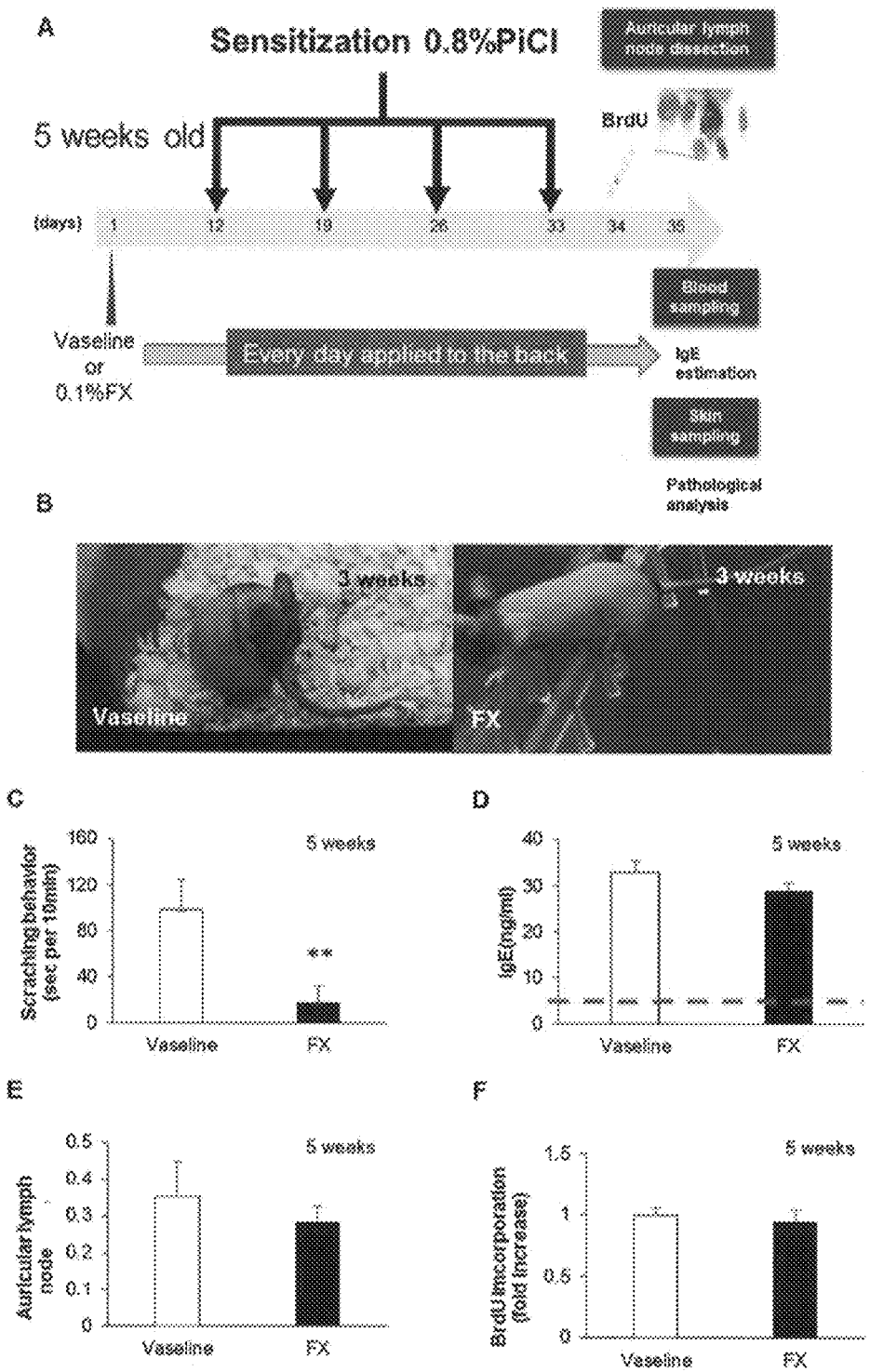
FIG. 1 shows itch suppression effect in fucoxanthin-treated NC/Nga mice. (A) Experimental protocols. Vaseline or fucoxanthin (0.1% FX in Vaseline) was applied to hair-removed back skin daily for 5 weeks. The mice were sensitized with 0.8% PiCl on day 12, day 19, day 26 and day 33. (B) Representative images of NC/Nga mouse after treatment with Vaseline (left) or fucoxanthin (right; FX) for 3 weeks. (C) The scratching behavior observed in Vaseline-treated mice (Vaseline) was attenuated in fucoxanthin-treated mice (FX) after treatment with Vaseline or fucoxanthin for 5 weeks. The vertical axis shows seconds spent for scratching behavior per 10 minutes. **: $p<0.01$ vs Vaseline-treated mice. (D) Biochemical analysis of serum IgE level. Each treated mice indicated similar IgE concentrations in blood samples that exceed the normal range (1-3 ng/ml) (dashed line). (E,F) Analysis of lymphedema. The length of auricular lymph node (cm) (E) and BrdU uptake (fold change vs Vaseline-treated mice) (F) were determined. Fucoxanthin (FX) failed to attenuate lymph inflammation compared to Vaseline control.

The present invention provides an agent for suppressing mast cell differentiation, comprising fucoxanthin or a derivative thereof, or a salt thereof.

Mast cell precursors develop from myeloid progenitor or granulocyte-monocyte progenitor cells (CMPs or GMPs). Following the expression of PU.1, which is a member of the ets transcription factor family, and the expression of GATA transcription factors, Cebpα expression is downregulated. Then, the CMPs or GMPs undergo differentiation into basophile/mast cell progenitors (BMCPs). Especially, GATA transcription factors are essential for maturation of mast cells. The BMCPs highly express Mitf1. The BMCPs terminally differentiate into basophils or mast cells. The mature mast cells express IgE receptors (FcεRI), and cause allergy and inflammation such as degranulation by antigen crosslinking by the FcεRI via IgE. The "mature mast cell" as used herein means a mast cell that expresses IgE receptors (FcεRI) and Hdc gene, which has tryptase-positive granules within the cell.

"Suppressing mast cell differentiation" as used herein includes inhibition of differentiation of bone marrow cells into mast cells, inhibition of differentiation of bone marrow cells into mast cell progenitors and inhibition of maturation of mast cells.

The agent for suppressing mast cell differentiation comprises fucoxanthin (CAS registration No. 3351-86-8) or a derivative thereof as an active ingredient. Examples of the derivatives of fucoxanthin include, but are not limited to, fucoxanthinol, a hydrolytic product thereof; amarouciaxanthin A, a resultant of dehydrogenation/isomerization of fucoxanthinol; a monoester of fucoxanthin selected from esters with amino acids such as glycine, alanine and the like, esters with carboxylic acids such as acetic acid, citric acid and the like and salts thereof, esters with inorganic acids such as phosphoric acid, sulfuric acid and the like and salts thereof, fatty acid esters with highly unsaturated fatty acids such as eicosapentaenoic acid, docosahexaenoic acid and the like, unsaturated fatty acids such as oleic acid, linoleic acid and the like, and saturated fatty acids such as palmitic acid, stearic acid and the like, etc; a diester of fucoxanthin having the same or different ester groups; and a glycoside such as glucoside and the like. These compounds may be chemically synthesized or extracted from natural products such as plants, animals, microorganisms and the like. The kinds, locality and production method of the starting material of fucoxanthin or a derivative thereof are not limited. Fucoxanthin or a derivative thereof may be used alone or two or more kinds thereof may be used in combination.

Examples of the salts of fucoxanthin or a derivative thereof may include inorganic acid salts such as hydrochloride, hydrobromide, sulfate, hydroiodide, nitrate, phosphate and the like; organic acid salts such as citrate, oxalate, acetate, formate, propionate, benzoate, trifluoroacetate, maleate, tartrate, methanesulfonate, benzenesulfonate, p-toluenesulfonate and the like; inorganic base salts such as sodium salt, potassium salt, calcium salt, magnesium salt, ammonium salt and the like; organic base salts such as triethylammonium salt, triethanolammnonium salt, pyridinium salt, diisopropylammonium salt and the like; and amino acid salts such as arginine salt, aspartate, glutamate and the like.

The active ingredient contained in the agent for suppressing mast cell differentiation of the present invention is preferably fucoxanthin or fucoxanthinol, more preferably fucoxanthin.

Fucoxanthin is a known compound and can be obtained by methods known per se. Fucoxanthin can be extracted from, for example, brown algaes such as brown seaweed and other Heterokontophyta, isolated and purified by methods known per se. Examples of the methods of preparing fucoxanthin include, but are not limited to, the method described in JP 2008-162 A, the method described in the Examples to be hereinafter described and the like.

Fucoxanthinol is also a known compound and can be produced by, for example, hydrolyzing fucoxanthin by a lipolytic enzyme such as lipase, cholesterol esterase or the like, and by the method described in JP 2009-33970 A, but the method is not limited thereto.

Since fucoxanthin, derivatives thereof and salts thereof (hereinafter sometimes to be referred to as "fucoxanthins") have effects including the following (1) to (7):
(1) inhibiting differentiation of bone marrow cells into GATA-1/GATA-2-positive mast cell progenitors;
(2) inhibiting granule formation in mast cells;
(3) inhibiting proliferation of mast cells;
(4) suppressing the expression of Hdc gene in mast cells;
(5) inhibiting formation of tryptase-positive granules in mast cells;
(6) inhibiting formation of toluidine blue-positive granules in mast cells; and
(7) suppressing degranulation of mast cells,
the fucoxanthins are effective to treat and prevent mast cell-mediated diseases. Examples of the mast cell-mediated diseases include diseases caused by increase of mast cells, diseases caused by abnormality in mast cell differentiation and the like. However, since the fucoxanthins are metabolized in liver and act as vitamin A-like substances, when they are taken orally, the agent for suppressing mast cell differentiation of the present invention is particularly useful for treating or preventing diseases to which topical administration is applicable, since the fucoxanthins per se can act as an active ingredient. Examples of the diseases to which topical administration is applicable include, but are not limited to, atopic dermatitis, hives, cutaneous mastocytosis, psoriasis, pruritus, asthma, rhinitis, conjunctivitis, keratoconjunctivitis, mastocytic leukemia, systemic mastocytosis, food allergy, basal cell carcinoma, squamous cell carcinoma, allergic rhinitis, allergic conjunctivitis, allergic and non-allergic bronchial asthmas, hyperretinoic acidosis and the like.

Preferably, as target diseases of the agent for suppressing mast cell differentiation of the present invention, mast cell-mediated disease associated with itch, especially dermal diseases, are exemplified. Accordingly, in a preferred embodiment, the present invention also provides an agent for suppressing itch comprising one or more fucoxanthins.

The agent for suppressing mast cell differentiation of the present invention can be topically administered (e.g., external administration such as application, spray, immersion and the like, ocular instillation, rhinenchysis, inhalation, aspiration, topical injection and the like) to a human or other mammal, for example, as a cosmetic, a drug, a quasi-drug or the like. For example, when the agent for suppressing mast cell differentiation of the present invention is used as a cosmetic, a drug or quasi-drug for external use or the like, it can be prepared in the form of ointment, lotion, spray, aerosol spray, cream, cleanser, composition for clean hot water to be used outside a bathtub, bath additive, ophthalmic ointment, eye drop, nasal drop, injectable form and the like. As mentioned above, since the agent for suppressing mast cell differentiation of the present invention is used as an agent for suppressing itch in dermal diseases in a preferred embodiment, it is preferably formulated into an external preparation for skin.

The agent for suppressing mast cell differentiation of the present invention can comprise other ingredients typically applicable to a cosmetic, a drug or a quasi-drug. As these optional ingredients, vitamins, pigments, inorganic salts, oily bases, surfactants, antiseptics, fragrances and the like are exemplified. The vitamins include retinol, thiamine, riboflavin, pyridoxine, cyanocobalamin, ascorbic acid, cholecalciferol, carnitine, orotic acid and the like. The pigments include Food Red No. 106, Food Blue No. 1, Orange No. 205, Yellow No. 202-(1), Yellow No. 203, FD & C Green No. 3 and the like. The inorganic salts include sodium sulfate, sodium hydrogencarbonate, sodium carbonate, sodium chloride, magnesium sulfate, aluminum sulfate, magnesium carbonate, potassium chloride, alum and the like. The oily bases include liquid lanolin, jojoba oil, rice germ oil, olive oil, Macadamia nut oil, scwaran, glyceryl tri(2-ethylhexanoate), isopropyl myistate, Vaseline, liquid paraffin and the like. The surfactants include sodium lauryl sulfate, sodium polyoxyethylene laurylether sulfate, lauric acid diethanolamide, polyoxyethylene glycol monostearate and the like. Furthermore, the agent for suppressing mast cell differentiation of the present invention may include water (purified water, hot spring water, deep water and the like), metal soap, gelator, powder, alcohols, water-soluble polymer, film forming agent, resin, ultraviolet protector, inclusion compound, deodorant, pH adjuster, algefacient, extract from animal or microorganism, plant extract, blood flow accelerator, astringent, antiseborrheic agent, lightening agent, anti-inflammatory agent, reactive oxygen species scavenger, cellular stimulant, moisturizer, chelating agent, keratolytic agent, enzyme, hormones, vitamins and the like.

A pharmaceutical composition suitable for topical administration can be produced using known formulation methods.

For example, when an ointment is to be formulated, it may be an oleaginous ointment or a water-soluble ointment, unless it fails to provide a desired effect. When an ointment is prepared, it may contain an ointment base in addition to the fucoxanthins. Examples of the ointment base generally include, but are not limited to, hydrocarbons, fatty acid esters, waxes, higher fatty acids, higher alcohols, water, polyols, lower alcohols and the like. To be specific, yellow petrolatum, white petrolatum, liquid paraffin, isopropyl myristate, paraffin, plastibase, silicone, beeswax, lanoline, glycerin, propylene glycol, 1,3-butylene glycol and mixtures thereof and the like are exemplified, but examples are not limited thereto.

When a cream is to be formulated, it may be a water-in-oil (W/O) type cream or an oil-in-water (O/W) type cream, unless it fails to provide a desired effect. When a cream is prepared, it may contain an emulsion base in addition to the fucoxanthins. Examples of the emulsion base generally include, but are not limited to, hydrocarbons, fatty acid esters, waxes, higher fatty acids, higher alcohols, water, polyols, lower alcohols and the like. To be specific, yellow petrolatum, white petrolatum, liquid paraffin, isopropyl myristate, paraffin, plastibase, silicone, beeswax, lanoline, glycerin, propylene glycol, 1,3-butylene glycol and mixtures thereof and the like are exemplified but examples are not limited thereto. The cream may further contain preservative, antioxidant, pH adjuster, surfactant and the like.

When a lotion is to be formulated, it may contain an ointment base in addition to the fucoxanthins. Examples of the ointment base generally include, but are not limited to, hydrocarbons, fatty acid esters, waxes, higher fatty acids, higher alcohols, water, polyols, lower alcohols and the like. To be specific, yellow petrolatum, white petrolatum, liquid paraffin, isopropyl myristate, paraffin, plastibase, silicone, beeswax, lanoline, glycerin, propylene glycol, 1,3-butylene glycol and mixtures thereof and the like are exemplified but examples are not limited thereto. The lotion may further contain preservative, antioxidant, pH adjuster, surfactant and the like.

When an injectable form is to be formulated, pH adjuster, buffer, stabilizer, isotonizing agent, local anesthetic agent and the like are added to the fucoxanthins to produce a subcutaneous, intramuscular or intravenous injection. The pH adjuster and buffer include, for example, sodium citrate, sodium acetate, sodium phosphate and the like. The stabilizer includes, for example, sodium pyrosulfite, EDTA (edetate disodium), thioglycolic acid, thiolactic acid and the like. The local anesthetic agent includes, for example, procaine hydrochloride, lidocaine hydrochloride and the like. The isotonizing agent includes, but is not limited to, for example, sodium chloride, glucose and the like.

When an ophthalmic ointment is to be prepared, it may contain an ointment base in addition to the fucoxanthins. Examples of the ointment base generally include, but are not limited to, hydrophobic bases such as oils, waxes, hydrocarbons and the like. To be specific, mineral bases such as yellow petrolatum, white petrolatum, paraffin, liquid paraffin, plastibase, silicone and the like, animal and plant bases such as beeswax, animal and plant oils and the like are exemplified but examples are not limited thereto.

When a suppository is to be formulated, to the fucoxanthins is added a known suppository base, for example, polyethylene glycol, lanoline, cocoa butter, fatty acid triglyceride or the like. A surfactant and the like are further added as appropriate. Then, the suppository is produced using a conventional method but the formulation method is not limited thereto.

The proportion of the fucoxanthins contained in the agent for suppressing mast cell differentiation of the present invention is not particularly limited and may be any as long as a single dose of the agent contains fucoxanthins in an amount sufficient for exerting suppressive effects on mast cell differentiation and itch. The agent for suppressing mast cell differentiation of the present invention may contain, for example, 0.0001 to 100 weight %, preferably 0.001 to 10 weight %, of the fucoxanthins. In the case of an ointment, a finger tip unit (1 FTU), which is an amount of ointment squeezed out in the length of from the tip to the first joint of an index finger, is approximately 0.5 g, and this amount is considered to be suitable for applying to the palm and fingers of both hands (i.e. two handprints; approximately 150 cm$^2$× 2). Therefore, the fucoxanthins can be contained in such amount that corresponds to the following proportion in 0.5 g of the whole preparation.

The dose of the agent for suppressing mast cell differentiation of the present invention varies depending on the patient's age, body weight and symptoms, dosing form, administration frequency and the like. For example, in the case of an ointment, the daily dose of fucoxanthins is typically 0.01 to 1,000 mg/two handprints (approximately 150 cm$^2$×2), preferably 0.1 to 100 mg/two handprints, more preferably 0.1 to 10 mg/two handprints, which can be applied to the affected area of an adult human once per day or in several divided portions per day.

The agent for suppressing mast cell differentiation of the present invention may further contain other active ingredients, for example, antihistamines (e.g., diphenhydramine hydrochloride, chlorpheniramine maleate, epinastine hydrochloride, fexofenadine hydrochloride and the like), immunosuppressants (e.g., tacrolimus, suplatast tosylate and the like), steroids (e.g., betamethasone valerate, triamcinolone acetonide, beclomethasone dipropionate, prednisolone acetate, fluorometholone and the like), suppressants for the release of chemical mediators (e.g., tranilast and the like) and the like, unless an undesired interaction occurs when combined with the fucoxanthins. As such other active ingredients, various drugs known per se can be used as appropriate. Alternatively, the other active ingredients and the agent of the present invention may be separately formulated, and administered to the same subject simultaneously or sequentially by the same route or different routes.

The present invention is hereinafter described in further detail by means of the following Examples; however, they are mere exemplifications, and the present invention is never limited thereto.

EXAMPLES

Example 1

Extraction of Fucoxanthin from Brown Seaweed

Seaweed roots were demineralized, dried and powderized. This powder (200 g) was extracted twice with methanol (1.5 L), and the solvent (total 3 L) was evaporated to give a residue (1 batch). The residue was separated by hexane two-phase partitioning and concentrated by evaporation. This residue from hexane was subfractionated on silica gel chromatography. Fucoxanthin was isolated and purified by thin layer chromatography and high performance liquid chromatography using a photodiode array detector.

Example 2

Itch Suppression Effect of Fucoxanthin in NC/Nga Mice

Using NC/Nga mice known as a model of atopic dermatitis (AD), the effect of fucoxanthin (FX) on atopic dermatitis was examined.

NC/Nga mice spontaneously develop dermatitis by parasitism of ticks and show symptoms very similar to atopic dermatitis such as pruritus, rubor, edema, excoriation, erosion, scabbing and dryness. These atopic dermatitis (AD)-like symptoms are also induced by repeated application of picryl chloride (PiCl) to the same site of NC/Nga mice skin.

NC/Nga mice (5 weeks old, female) were purchased from Japan SLC, Inc. As shown in FIG. 1A, Vaseline or Vaseline containing 0.1% (w/w) fucoxanthin (500 mg) was applied daily to the back skin of the mice for 5 weeks. On day 12, day 19, day 26 and day 33 after starting application of Vaseline or fucoxanthin, 0.8% picryl chloride (PiCl) was further applied to the back skin of the mice. The behaviors of the mice were observed by video monitoring. On day 34 after starting application of Vaseline or fucoxanthin, bromodeoxyuridine (BrdU, Nacalai Tesque) (0.125 g/g weight) was intraperitoneally administered to the mice. At 5 weeks after starting application of Vaseline or fucoxanthin, the time each mouse spent for scratching behavior in 10 minutes was measured by video monitoring. Then, the mice were sacrificed and the auricular lymph node, blood and skin were obtained. Serum IgE content was determined by enzyme-linked immunosorbent assay (ELISA) using Mouse IgE Assay Kit (Morinaga Institute of Biological Science, Inc.). The auricular lymph node was digested with 0.1% trypsin/0.1% collagenase, the obtained dissociated cells were suspended by pipetting, and the enzyme reaction was stopped by adding Dulbecco's modified Eagle medium (DMEM) containing 10% fetal bovine serum (Wako Pure Chemical Industries, Ltd.). BrdU uptake was determined by ELISA using Cell Proliferation ELISA, BrdU (Colorimetric) (Roche Diagnostics K.K.).

Immediately after starting the application, no difference was observed between the Vaseline-applied mice and the fucoxanthin-applied mice. However, at 5 weeks after starting application, difference in the time spent for scratching behavior was observed between the Vaseline-applied mice and the fucoxanthin-applied mice (FIG. 1C). We found that the time spent by the fucoxanthin-applied mice for scratching behavior was remarkably shorter than the time spent by the Vaseline-applied mice. On the other hand, serum IgE level did not vary in both mice (FIG. 1D). Also, swelling of the auricular lymph node and BrdU uptake were not affected by the application of fucoxanthin (FIGS. 1E and 1F).

These results demonstrate that topical application of fucoxanthin suppresses scratching behavior, namely itch in dermatitis model mice. However, in spite of the significant impact on the mice behavior, fucoxanthin did not affect serum IgE level, and swelling of and cell proliferation in the auricular lymph node. These results suggest that fucoxanthin affects immune cells locally rather than systemically.

Example 3

Reduction of the Number of Mast Cells by Application of Fucoxanthin

Next, we examined the effect of application of fucoxanthin on mast cells.

In the same manner as described in Example 2, Vaseline or fucoxanthin and PiCl were applied to NC/Nga mice. At 5 weeks after starting application of Vaseline or fucoxanthin, the mice were sacrificed, the mice skins were fixed with 4% paraformaldehyde and embedded in paraffin. The skin specimen was stained with toluidine blue (TB) (pH=4.1). Imaging of the stained specimen was performed by Virtual Slide System (Olympus).

Figure 2:
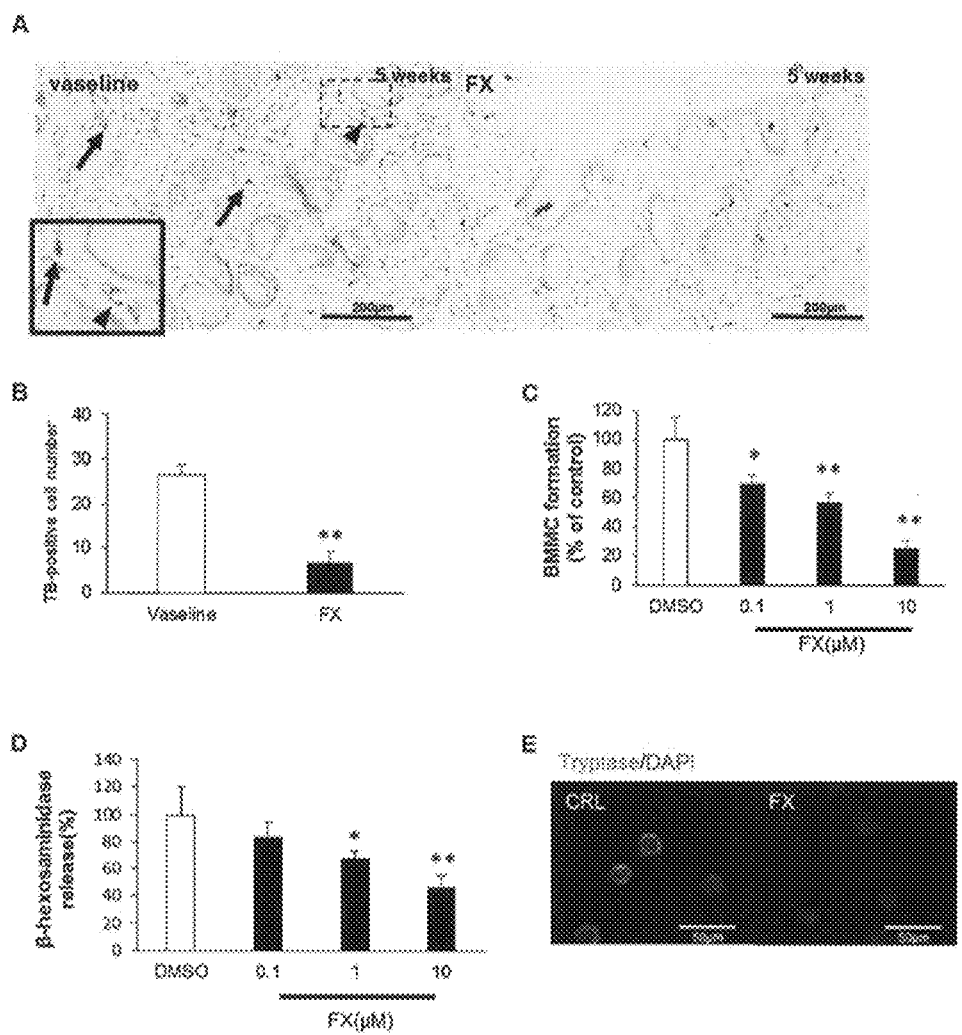
FIG. 2 shows that fucoxanthin inhibits both maturation and degranulation of mast cells in vitro and in vivo. (A) Toluidine blue (TB) staining of the skin specimens from 0.1% fucoxanthin-treated (right; FX) and Vaseline-treated (left; Vaseline) NC/Nga mice. Skins from the NC/Nga mice were fixed in 4% paraformaldehyde, and were embedded in paraffin. Arrows indicate TB-positive cells, arrowheads indicate degranulation of mast cells. Solid line box is a magnification of dashed line box. (B) The number of TB-positive cells in skin from 0.1% fucoxanthin-treated (FX) or Vaseline-treated (Vaseline) NC/Nga mice was calculated from 3 fields (1 mm×1.5 mm) per one sample. (n=5) **: $p<0.01$. (C) Number of bone marrow-derived mast cells (BMMCs). Bone marrow cells were treated with fucoxanthin (0.1 µM, 1 µM, 10 µM). The number of BMMCs was calculated from ten fields (100 µm×100 µm) per well. *: $p<0.05$, **: $p<0.01$. (D) Inhibition of degranulation of BMMCs by fucoxanthin. Bone marrow cells were incubated in a medium for conditioning containing interleukin-3 (IL-3) for 4 weeks. Then, degranulation was triggered by the addition of an anti-dinitrophenyl (DNP)-IgE antibody. The BMMCs were treated with fucoxanthin (FX) or dimethylsulfoxide (DMSO) for 30 minutes before Fc receptor stimulation. *: $p<0.05$, **: $p<0.01$. (E) Granule formation in BMMCs. Immunohistochemical analysis was performed using BMMCs treated with 10 µM Vaseline (left; CRL) or 10 µM fucoxanthin (right; FX). No tryptase-positive cell (green) was observed in fucoxanthin-treated cells. The number of cells was counted by counter staining with DAPI (Blue).

The number of toluidine blue (TB)-positive cells in the fucoxanthin-applied mice was remarkably lower than that in the Vaseline-applied mice (FIGS. 2A and 2B).

These results suggest that fucoxanthin reduces the number of mast cells having granules.

Example 4

Suppression of the Formation of Bone Marrow-Derived Mast Cells (BMMCs) by Fucoxanthin Next, we studied on the effect of fucoxanthin on maturation of mast cells (BMMCs).

Bone marrow cells were obtained from 8-week-old female mice and cultured in a medium for conditioning that contained WEHI-3 cells (National Institute of Biomedical Innovation, Health and Nutrition). The culture was performed according to the method described in Yamashita, U. et al. (2005) "Strain difference of murine bone marrow-derived mast cell functions." *J. Leukoc. Biol.* 78(3): 605-611. The bone marrow cells were treated with 0.1 µM, 1 µM or 10 µM fucxanthin, or dimethyl sulfoxide (DMSO) as a control. The number of BMMCs containing 10 fields (100 µm×100 µm) per well was counted (FIG. 2C).

BMMCs were formed from bone marrow cells by culturing them in the medium for conditioning containing WEHI-3 cells (National Institute of Biomedical Innovation, Health and Nutrition). Fucoxanthin suppressed BMMC formation in a dose-dependent manner.

Example 5

Suppression of Degranulation of Bone Marrow-Derived Mast Cells (BMMCs) by Fucoxanthin Next, we studied on the effect of fucoxanthin on degranulation of mast cells (BMMCs).

The degranulation of BMMCs was evaluated by measuring β-hexosaminidase activity in the culture solution of the mature mast cells. Bone marrow cells obtained from 8-week-old female mice were cultured in a medium for conditioning containing interleukin-3 (IL-3) for 4 weeks to give mature mast cells. The mature mast cells thus prepared were cultured in 24-well plate ($5 \times 10^3$ cells/well) overnight, and sensitized with 50 ng/mL anti-DNP-IgE (Sigma Chemicals) at 37° C. for 2 hours. The cells were rinsed by MT buffer (137 mmol/L NaCl, 2.7 mmol/L KCl, 1.8 mmol/L $CaCl_2$, 1 mmol/L $MgCl_2.6H_2O$, 5.6 mmol/L glucose, 20 mmol/L HEPES, 0.1% BSA, pH7.3), and pre-treated with 0.1 μM, 1 μM or 10 μM fucoxanthin, or dimethyl sulfoxide (DMSO) for 10 minutes. Then, the cells were treated with 2.5 μg/mL DNP-labeled human serum albumin (Sigma Chemicals) at 37° C. for 30 minutes. After incubation, the supernatant was transferred to a 96-well plate and incubated with 3.3 mM p-nitrophenyl-2-acetamide-2-deoxy-β-glucopyranoside at 37° C. for 25 minutes. Absorbance at 405 nm was measured using microplate reader. The results are shown as percentage of total β-hexosaminidase.

The results are shown in FIG. 2D. The mature mast cells treated with 0.1 μM, 1 μM or 10 μM fucoxanthin released less amount of β-hexosaminidase as compared to the DMSO-treated cells. Fucoxanthin suppressed release of β-hexosaminidase in a dose-dependent manner.

Example 6

Suppression of Granule Formation in Bone Marrow-Derived Mast Cells (BMMCs) by Fucoxanthin To clarify the effect of fucoxanthin on granule formation in mast cells, immunostaining of tryptase, which is a granule marker of mast cells, was performed.

Mature mast cells were prepared in the same manner as described in Example 5. The BMMCs obtained were mounted on a glass slide and heat-fixed. The analysis of the preparation was performed according to the method described in Kosaka, T., Fukui, R., Matsui, M. et al. (2014) "RAGE, Receptor of Advanced Glycation Endoproducts, Negatively Regulates Chondrocytes Differentiation." *PLoS ONE* 9(10): e108819. Briefly, the cells were reacted with a mouse anti-mast cell tryptase antibody (AB2378, Abcam, Tokyo, Japan) and then reacted with an FITC-conjugated anti-mouse IgG (Santa Cruz Biotechnology, Inc.) and 1 μg/mL DAPI (4',6-diamino-2-phenylindole dihydrochloride). The fluorescent image was analyzed by EVOS® FL Cell Imaging System (Life Technologies Corp).

Only a little immunoreactivity against tryptase was observed in the mature mast cells treated with 10 μM fucoxanthin as compared to the Vaseline-treated cells. Namely, the results of immunostaining analysis using an anti-tryptase antibody revealed that fucoxanthin almost completely inhibited granule formation in the mast cells (FIG. 2E).

These results demonstrate that fucoxanthin treatment directly or locally reduces itch associated with atopic dermatitis (AD) by inhibiting maturation and degranulation of mast cells.

Example 7

Changes in Gene Expression by Fucoxanthin Treatment

To study whether fucoxanthin affects the expression of transcription factors related to mast cell differentiation, we examined changes in gene expression of these transcription factors by real time PCR.

Bone marrow cells obtained from 8-week-old female mice was cultured in a medium for conditioning containing IL-3. On the day the bone marrow cells were obtained (day 0), 10 μM fucoxanthin or dimethyl sulfoxide (DMSO) as a control was added to the culture solution and the cells were cultured for 1, 2, 3 or 4 weeks. Quantitative real time PCR was performed according to the method described in Kosaka et al. (supra). Five different cDNA pool dilutions were used for the experiments. The expression levels of PCR products were normalized to that of a housekeeping gene, GAPDH or β-actin, and the measured values were compared with cycle threshold value (Ct value). The primers used are shown below.

```
                                        (SEQ ID NO: 1)
GAPDH-F:    5'-TGCACCACCAACTGCTTAG-3'

(SEQ ID NO: 2)
GAPDH-R:    5'-GGATGCAGGGATGATGTTC-3'

(SEQ ID NO: 3)
β-actin-F:  5'-AGCCTCGCCTTTGCCGATCC-3'

(SEQ ID NO: 4)
β-actin-R:  5'-TTGCACATGCCGGAGCCGTT-3'

(SEQ ID NO: 5)
GATA-1-F:   5'-CGCTCCCTGTCACCGGCAGTGC-3'

(SEQ ID NO: 6)
GATA-1-R:   5'-CCGCCACAGTGGAGTAGCCGTT-3'

(SEQ ID NO: 7)
GATA-2-F:   5'-CTCCCGACGAGGTGGATGTCTT-3'

(SEQ ID NO: 8)
GATA-2-R:   5'-CCTGGGCTGTGCAACAAGTGTG-3'

(SEQ ID NO: 9)
Mitf1-F:    5'-AGCAACGAGCTAAGGACC-3'

(SEQ ID NO: 10)
Mitf1-R:    5'-GGATGGGATAAGGGAAAGT-3'

(SEQ ID NO: 11)
PU.1-F:     5'-TGICCACAACAACGAG-3'

(SEQ ID NO: 12)
PU.1-R:     5'-GGGACAAGGTTTGATA-3'

(SEQ ID NO: 13)
FcεR1α-F:   5'-TGCCACCGTTCAAGACAG-3'

(SEQ ID NO: 14)
FcεR1α-R:   5'-TTGCGGACATTCCAGTTC-3'

(SEQ ID NO: 15)
Hdc-F:      5'-GAGCCCGATGCTAATGAGTC-3'
```

-continued

|  | (SEQ ID NO: 16) |
|---|---|
| Hdc-R: | 5'-GAGAAGTTGTCGTCCACAGGTA-3' |

|  | (SEQ ID NO: 17) |
|---|---|
| Cebpα-F: | 5'-GCATCTGCGAGCACGAGACGCT-3' |

|  | (SEQ ID NO: 18) |
|---|---|
| Cebpα-R: | 5'-CGCCTTGGCCTTCTCCTGCTGT-3' |

The housekeeping genes GAPDH and β-actin were used for normalization as internal standards. All measurements were performed 4 times.

Figure 3:
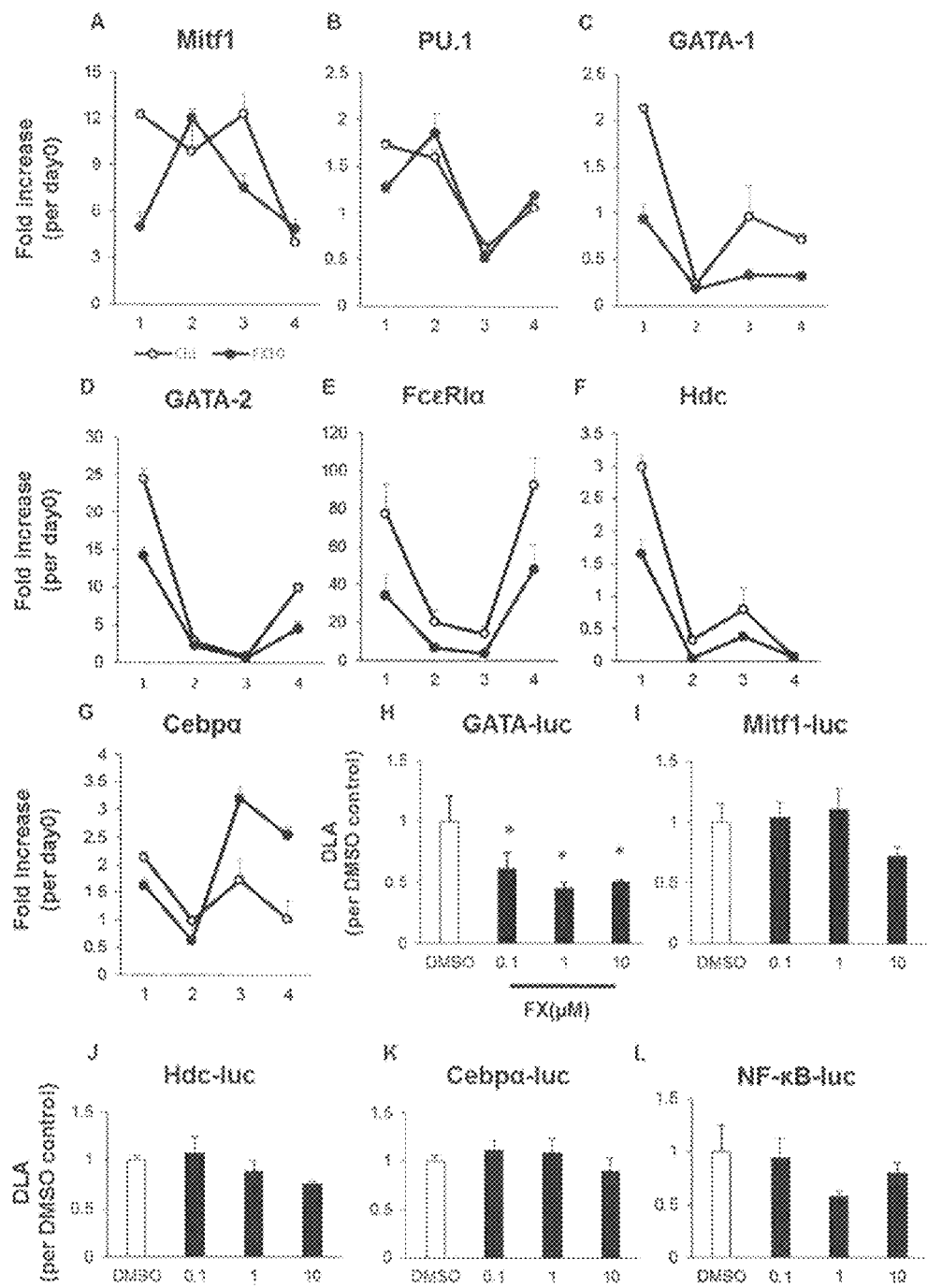
FIG. 3 shows regulation of mast cell differentiation by fucoxanthin. (A-G) The expression levels of Mitf1 (A), PU.1 (B), GATA-1 (C), GATA-2 (D), FcεRIα (E), Hdc (F) and Cebpα (G) in bone marrow cells incubated in a medium for conditioning containing IL-3 for 1-4 weeks. Ten micromolar of fucoxanthin (FX10; filled circle) or dimethylsulfoxide (DMSO) (CRL; open circle) was added on the day bone marrow was obtained (day 0). (C-F) Fucoxanthin downregulated GATA-1, GATA-2, FcεRIα and Hdc. (G) Cebpα was upregulated by fucoxanthin at 3 weeks later. (H-L) Reporter assay of GATA-luc (H), Mitf1-luc (I), Hdc-luc (J), Cebpα-luc (K) and NFκB-luc (L). HEK293 cells were transfected with each of the reporter vectors and treated with fucoxanthin (0.1 µM, 1 µM, 10 µM) or DMSO 3 hours after transfection. Only GATA expression was downregulated by fucoxanthin. *: $p<0.05$ vs DMSO control. The values indicate the mean of 4 wells±standard error.

The results are shown in FIGS. 3A to 3G. As shown in FIGS. 3A and 3B, the expression of Mitf1 and PU.1 did not change significantly in all stages. However, GATA-1, GATA-2, FcεRIα (mast cell and basophil markers) and histidine decarboxylase (Hdc) were downregulated by fucoxanthin (FIGS. 3C to 3F). While Cebpα was downregulated by fucoxanthin for the first 2 weeks, it was remarkably upregulated by fucoxanthin during 3 to 4 weeks after starting culture (FIG. 3G).

In particular, GATA transcription factors are involved in mast cell differentiation at the early stage, whereas Cebpα is an important switching factor for mast cell differentiation at the later stage (Rao, K. N. et al. (2013) *Blood* 122(15): 2572-2581).

Therefore, these data suggest that fucoxanthin directly inhibits maturation of mast cells by acting on GATA transcription factors.

Example 8

Reporter Assay Using Fucoxanthin-Treated Cells

To confirm the results of Example 7, reporter assay was performed using a reporter vector fused with three tandemly linked GATA-responsive elements.

The plasmids pGL3-Cebpα promoter-luc and pGL3-Mitf1 promoter-luc were provided by Dr. Hua Huang (University of Colorado school, Denver, USA). The plasmid NF-κB-luc was purchased from Agilent Technologies (Santa Clara, Calif.). The GATA-responsive reporter vector was provided by Dr. Ishijima (Takasaki University of Health and welfare, Gunma, Japan). Three GATA motifs from mouse α-1 globulin gene (5'-TGATAA-3') were tandemly inserted into Sma I site of pRBGP3. HDC promoter was provided by Dr. Ootsu (Tohoku University school of Medicine, Sendai, Japan) and cloned into Kpn I-Hind III site of pGL4.10 (Hdc promoter-luc). The reporter assay was performed according to the method described in Kanatani, N. et al. Briefly, HEK293 cells were transfected with each of the luciferase constructs (0.2 μg) or pRL-CMV (Promega, Madison, Wis.) (0.001 μg). At 3 hours after transfection, the cells were treated with fucoxanthin (0.1 μM, 1 μM or 10 μM) or DMSO for 48 hours and reporter assay was performed using Dual-Luciferase® Reporter Assay System (Promega). Luciferase activity was measured using luminometer model TD20/20n (Turner BioSystems, Sunnyvale, Calif.) and normalized to Renilla luciferase activity expressed by CMV promoter.

The results are shown in FIGS. 3H to 3L. Mitf1-luc, Hdc-luc and Cebpα-luc were not regulated by fucoxanthin (FIGS. 3I to 3K). While it has been reported that inhibition of NF-κB leads to reduction of Hdc induction, NF-κB activity was not affected by fucoxanthin (FIG. 3L). Only GATA-luc was downregulated by fucoxanthin treatment (FIG. 3H).

Example 9

Immunohistochemical Analysis of Filaggrin Induction by Fucoxanthin

Immunohistochemical analysis of filaggrin (Flg) and loricrin (Lor) was performed using NC/Nga mice treated with Vaseline or focoxanthin.

Vaseline or fucoxanthin and PiCl were applied to the mice in the same manner as described in Example 2. At 5 weeks after starting application of Vaseline or fucoxanthin, the mice were sacrificed the mice skins were fixed with 4% paraformaldehyde and analyzed according to the method described in Kosaka, T. et al. (supra). The skin section (10 μm thick) was analyzed immunohistochemically using a rabbit anti-filaggrin antibody (Santa Cruz Biotechnology, Inc.) and a rabbit anti-loricrin antibody (Covance). Then, the sample was reacted with an FITC-conjugated anti-rabbit IgG IgG (Santa Cruz Biotechnology, Inc.).

Fucoxanthin induced the expression of filaggrin and loricrin in NC/Nga mice. After fucoxanthin treatment for 5 weeks, both expression levels of filaggrin (Flg) and loricrin (Lor) were elevated in the epidermis (FIGS. 4A to 4D). Filaggrin labeled by FITC was abundantly localized in the stratum corneum of fucoxanthin-treated skin, and loricrin was distributed in the whole skin treated with fucoxanthin.

Filaggrin is an important dermal barrier protein. Loricrin is also necessary for dermal barrier formation.

Example 10

Immunohistochemical Analysis of Filaggrin Induction by Fucoxanthin (2)

Next, semi-quantitative analysis by immunoblot was performed.

The immunoblot analysis was performed according to the method described in Kosaka, T. et al. (supra). Mice skin proteins were analyzed by SDS-10% polyacrylamide gel electrophoresis. The blots were incubated with a rabbit anti-filaggrin antibody (Santa Cruz Biotechnology, Inc., Santa Cruz, Calif.), a rabbit anti-actin antibody (Santa Cruz Biotechnology, Inc., Santa Cruz, Calif.) or a rabbit anti-loricrin antibody (Covance, Berkeley, Calif.), and then reacted with a horseradish peroxidase-conjugated anti-rabbit IgG or anti-donkey IgG (Santa Cruz Biotechnology, Inc.).

Figure 4:
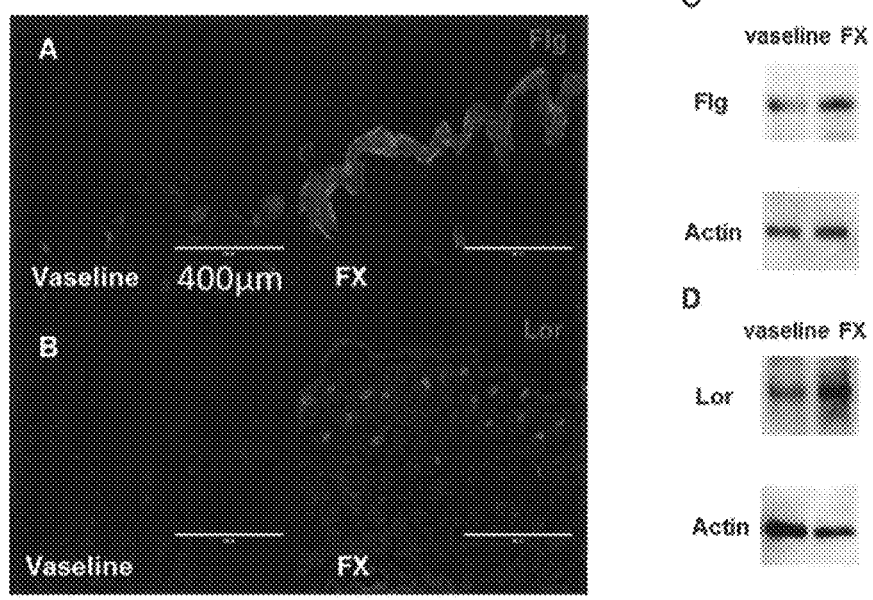
FIG. 4 shows that fucoxanthin induces filaggrin (Flg) expression in NC/Nga mice. (A,B) Fluorescent immunohistochemical analyses of filaggrin (Flg) (A) and loricrin (Lor) (B) in NC/Nga mice. Filaggrin (visualized by FITC) was abundantly localized in the stratum corneum of fucoxanthin-treated skin, and loricrin was distributed in the whole skin treated with fucoxanthin. (C,D) Semi-quantitative analysis by western blot. The expression levels of filaggrin and loricrin were elevated in the skins of fucoxanthin-treated NC/Nga mice.

The expression levels of filaggrin and loricrin were elevated in the skin of NC/Nga mice treated with fucoxanthin (FIGS. 4C and 4D).

Example 11

Reporter Assay Using Carotenoid-Treated Cells

GATA-reporter assay was performed using HEK293 cells expressing GATA-luc prepared in Example 8, in the same manner as described in Example 8 except using various carotenoids (fucoxanthin, astaxanthin, lycopene, β-carotene or retinoic acid) in place of fucoxanthin.

Figure 5:
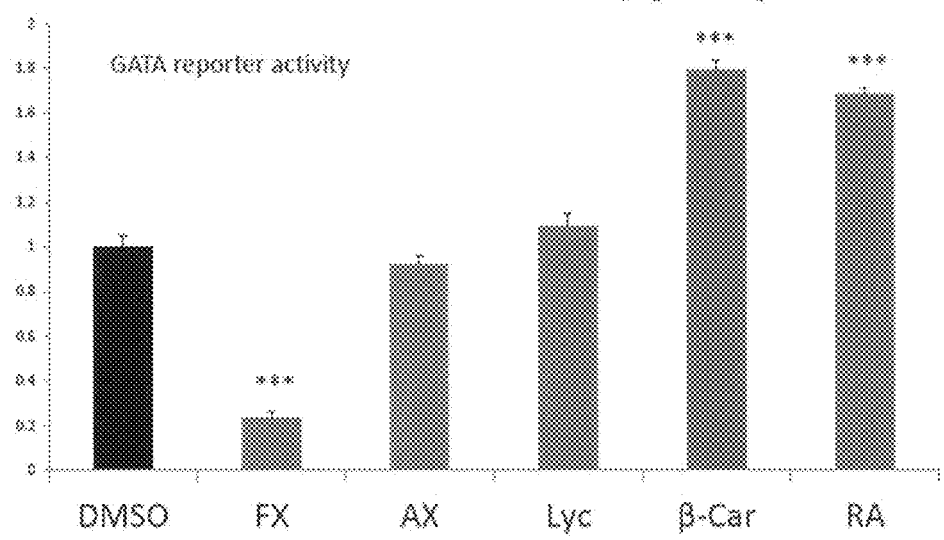
FIG. 5 shows suppressive effect of various carotenoids on GATA-reporter expression. GATA-luc expression was downregulated by fucoxanthin treatment (FX), whereas GATA-luc expression was not downregulated in astaxanthin-treated (AX) or lycopene-treated (Lyc) cells. In contrast, GATA-luc expression was upregulated in β-carotene-treated (β-Car) or retinoic acid-treated (RA) cells. ***: $p<0.001$ vs DMSO control.

The results are shown in FIG. 5. While fucoxanthin treatment downregulated GATA-luc expression, GATA-luc expression was not downregulated in astaxanthin- or lycopene-treated cells. On the other hand, GATA-luc expression was rather upregulated in β-carotene- or retinoic acid-treated cells.

Example 12

Comparison of Effects of Fucoxanthin and Astaxanthin on BMMCs and NC/Nga Mice

To confirm where the effect of fucoxanthin on granule formation in mast cells is specific rather than common to carotenoids, we compared granule formation between fucoxanthin-treated and astaxanthin-treated BMMCs by immunostaining of tryptase. The immunostaining assay was performed in the same manner as described in Example 6.

The results are shown in FIG. 6A. Tryptase-positive cells were remarkably reduced in the fucoxanthin-treated BMMCs, whereas tryptase-positive cells were not significantly reduced in astaxanthin-treated BMMCs.

Next, we examined the effects of fucoxanthin and astaxanthin on clinical symptoms of dermatitis in NC/Nga mice. In the same manner as described in Example 2, fucoxanthin or astaxanthin and PiCl were applied to NC/Nga mice. At 5 weeks after starting application of fucoxanthin or astaxanthin, clinical symptoms of dermatitis were observed in the mice.

The results are shown in FIG. 6B. The clinical symptoms of dermatitis were remarkably improved in the fucoxanthin-treated mice (left) as compared to the astaxanthin-treated mice (right).

Figure 7:
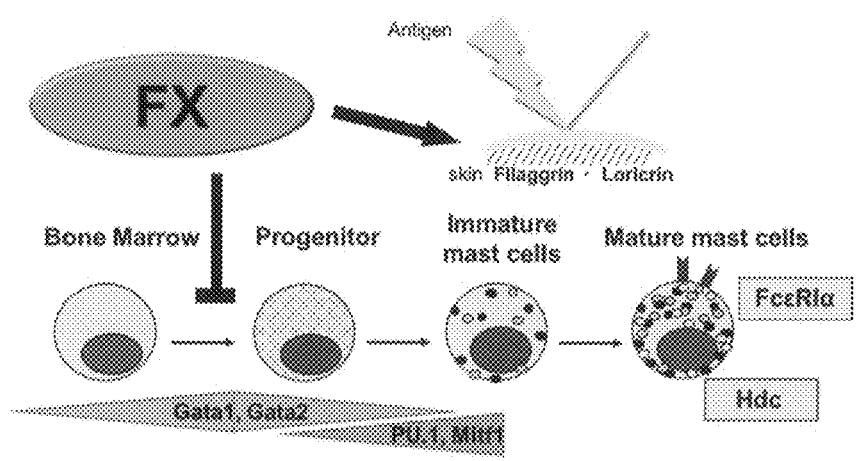
FIG. 7 shows two novel mechanisms of action of fucoxanthin against skin. Fucoxanthin (FX) induced dermal barrier proteins such as filaggrin and loricrin as well as decreased mast cell maturation and the suppression of granule formation in the mast cells and degranulation thereof.

From the above-mentioned Examples, it is suggested that fucoxanthin suppresses dermal diseases by improving the barrier function of the skin via induction of barrier proteins such as filaggrin and loricrin, as well as by inhibiting formation and function of mast cells (FIG. 7).

Example 13

Comparison of Fucoxanthin and Tacrolimus in the Effects on Skin Clinical Symptoms, Ear Swelling and Serum IgE Level in NC/Nga Mice Next, we compared the effects of fucoxanthin on the symptoms of dermatitis in NC/Nga mice with those of tacrolimus, which is an immunosuppressant widely used for the treatment of atopic dermatitis.

In the same manner as described in Example 2, Vaseline, fucoxanthin or tacrolimus and PiCl were applied to NC/Nga mice. At 5 weeks after starting application of Vaseline, fucoxanthin or tacrolimus, skin clinical symptoms of Vaseline-applied, fucoxanthin-applied and tacrolimus-applied mice were observed and compared. Also, serum IgE levels and swelling of the auricular lymph nodes of the mice were determined in the same manner as described in Example 2.

Figure 8:
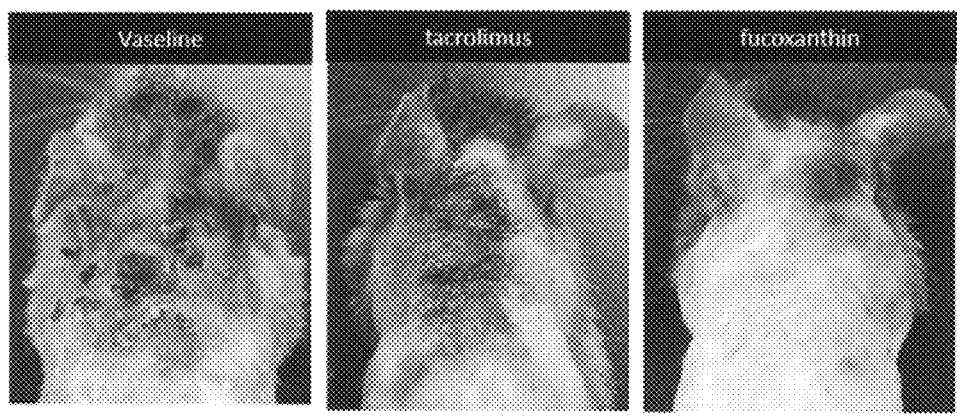
FIG. 8 shows comparison of fucoxanthin and tacrolimus in the effects on clinical symptoms of dermatitis in NC/Nga mice. The skin clinical symptoms in fucoxanthin-treated and tacrolimus-treated Nc/Nga mice at 5 weeks after starting treatment with respective compounds.

The results are shown in FIG. 8 and FIG. 9. While tacrolimus protected AD symptoms partially, fucoxanthin almost completely did (FIG. 8). On the other hand, neither ear swelling (FIG. 9A) nor serum IgE level (FIG. 9B) were affected by the application of fucoxanthin or tacrolimus.

These results clearly indicate that local treatment with either fucoxanthin or tacrolimus did not affect systemic immunological balance.

Example 14

Fucoxanthin is Faster-Acting than Tacrolimus on Itch in NC/Nga Mice

Next, we evaluated the fast-acting property of fucoxanthin on itch suppression and improvement of barrier function as compared to tacrolimus.

In the same manner as described in Example 2, Vaseline, fucoxanthin or tacrolimus and PiCl were applied to NC/Nga mice. At 5 weeks after starting application of fucoxanthin or tacrolimus, the time spent for scratching behavior per 10 minutes in the mice treated with fucoxanthin was measured and compared to that in the mice treated with tacrolimus. Transdermal water loss (TEWL) in the skin of the mice treated with fucoxanthin was also measured and compared with that in the skin of the mice treated with tacrolimus.

The results are shown in FIG. 10. Fucoxanthin (FX) was faster-acting than tacrolimus (FK) on itch in the mice (FIG. 10A). Fucoxanthin treatment (FX) remarkably inhibited moisture evaporation from the skin of NC/Nga mice, whereas tacrolimus (FK) did not affect TEWL in the mice.

These results suggest that the dual functionality of fucoxanthin shown in FIG. 7 conducive to its more fast-acting property compared to tacrolimus that lacks skin barrier function-improving action.

According to the present invention, mast cell differentiation can be suppressed and mast cell-mediated diseases can be treated and prevented. Therefore, the present invention provides a novel and effective means for treating and/or preventing mast cell-mediated diseases such as atopic dermatitis.

What is claimed is:

1. A method of suppressing mast cell differentiation in the skin of a subject, comprising topically administering to the skin in need thereof an effective amount of fucoxanthin, fucoxanthinol, amarouciaxanthin A, a monoester of fucoxanthin selected from esters with amino acids, esters with carboxylic acids and salts thereof, esters with inorganic acids and salts thereof, fatty acid esters with highly unsaturated fatty acids, unsaturated fatty acids, and saturated fatty acids, a diester of fucoxanthin having the same or different ester groups, or a glycoside.

2. A method of suppressing itch in the skin of a subject, comprising topically administering to the skin in need thereof an effective amount of fucoxanthin, fucoxanthinol, amarouciaxanthin A, a monoester of fucoxanthin selected from esters with amino acids, esters with carboxylic acids and salts thereof, esters with inorganic acids and salts thereof, fatty acid esters with highly unsaturated fatty acids, unsaturated fatty acids, and saturated fatty acids, a diester of fucoxanthin having the same or different ester groups, or a glycoside.

3. The method of claim 2, wherein fucoxanthin is administered to the skin.

4. The method of claim 2, wherein fucoxanthinol is administered to the skin.

5. The method of claim 2, wherein amarouciaxanthin A is administered to the skin.

6. The method of claim 2, wherein a monoester of fucoxanthin selected from esters with amino acids, esters with carboxylic acids and salts thereof, esters with inorganic acids and salts thereof, fatty acid esters with highly unsaturated fatty acids, unsaturated fatty acids, and saturated fatty acids is administered to the skin.

7. The method of claim 2, wherein a diester of fucoxanthin having the same or different ester groups is administered to the skin.

8. The method of claim 2, wherein a glycoside is administered to the skin.

9. The method of claim 1, wherein fucoxanthin is administered to the skin.

10. The method of claim 1, wherein fucoxanthinol is administered to the skin.

11. The method of claim 1, wherein amarouciaxanthin A is administered to the skin.

12. The method of claim 1, wherein a monoester of fucoxanthin selected from esters with amino acids, esters with carboxylic acids and salts thereof, esters with inorganic acids and salts thereof, fatty acid esters with highly unsaturated fatty acids, unsaturated fatty acids, and saturated fatty acids is administered to the skin.

13. The method of claim 1, wherein a diester of fucoxanthin having the same or different ester groups is administered to the skin.

14. The method of claim 1, wherein a glycoside is administered to the skin.

* * * * *

SEQUENCE LISTING

```
<160> NUMBER OF SEQ ID NOS: 18

<210> SEQ ID NO 1
<211> LENGTH: 19
<212> TYPE: DNA
<213> ORGANISM: Artificial Sequence
<220> FEATURE:
<223> OTHER INFORMATION: Primer

<400> SEQUENCE: 1
tgcaccacca actgcttag                                              19

<210> SEQ ID NO 2
<211> LENGTH: 19
<212> TYPE: DNA
<213> ORGANISM: Artificial Sequence
<220> FEATURE:
<223> OTHER INFORMATION: Primer
```

```
<400> SEQUENCE: 2
ggatgcaggg atgatgttc                                                  19

<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
agcctcgcct ttgccgatcc                                                 20

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
ttgcacatgc cggagccgtt                                                 20

<210> SEQ ID NO 5
<211> LENGTH: 22
<212> TYPE: DNA
<213> ORGANISM: Artificial Sequence
<220> FEATURE:
<223> OTHER INFORMATION: Primer

<400> SEQUENCE: 5
cgctccctgt caccggcagt gc                                              22

<210> SEQ ID NO 6
<211> LENGTH: 22
<212> TYPE: DNA
<213> ORGANISM: Artificial Sequence
<220> FEATURE:
<223> OTHER INFORMATION: Primer

<400> SEQUENCE: 6
ccgccacagt ggagtagccg tt                                              22

<210> SEQ ID NO 7
<211> LENGTH: 22
<212> TYPE: DNA
<213> ORGANISM: Artificial Sequence
<220> FEATURE:
<223> OTHER INFORMATION: Primer

<400> SEQUENCE: 7
ctcccgacga ggtggatgtc tt                                              22

<210> SEQ ID NO 8
<211> LENGTH: 22
<212> TYPE: DNA
<213> ORGANISM: Artificial Sequence
<220> FEATURE:
<223> OTHER INFORMATION: Primer

<400> SEQUENCE: 8
cctgggctgt gcaacaagtg tg                                              22

<210> SEQ ID NO 9
```

```
<211> LENGTH: 18
<212> TYPE: DNA
<213> ORGANISM: Artificial Sequence
<220> FEATURE:
<223> OTHER INFORMATION: Primer

<400> SEQUENCE: 9
agcaacgagc taaggacc                                                   18

<210> SEQ ID NO 10
<211> LENGTH: 19
<212> TYPE: DNA
<213> ORGANISM: Artificial Sequence
<220> FEATURE:
<223> OTHER INFORMATION: Primer

<400> SEQUENCE: 10
ggatgggata agggaaagt                                                  19

<210> SEQ ID NO 11
<211> LENGTH: 16
<212> TYPE: DNA
<213> ORGANISM: Artificial Sequence
<220> FEATURE:
<223> OTHER INFORMATION: Primer

<400> SEQUENCE: 11
tgtccacaac aacgag                                                     16

<210> SEQ ID NO 12
<211> LENGTH: 16
<212> TYPE: DNA
<213> ORGANISM: Artificial Sequence
<220> FEATURE:
<223> OTHER INFORMATION: Primer

<400> SEQUENCE: 12
gggacaaggt ttgata                                                     16

<210> SEQ ID NO 13
<211> LENGTH: 18
<212> TYPE: DNA
<213> ORGANISM: Artificial Sequence
<220> FEATURE:
<223> OTHER INFORMATION: Primer

<400> SEQUENCE: 13
tgccaccgtt caagacag                                                   18

<210> SEQ ID NO 14
<211> LENGTH: 18
<212> TYPE: DNA
<213> ORGANISM: Artificial Sequence
<220> FEATURE:
<223> OTHER INFORMATION: Primer

<400> SEQUENCE: 14
ttgcggacat tccagttc                                                   18

<210> SEQ ID NO 15
<211> LENGTH: 20
<212> TYPE: DNA
<213> ORGANISM: Artificial Sequence
<220> FEATURE:
<223> OTHER INFORMATION: Primer

<400> SEQUENCE: 15
```

```
gagcccgatg ctaatgagtc                                              20

<210> SEQ ID NO 16
<211> LENGTH: 22
<212> TYPE: DNA
<213> ORGANISM: Artificial Sequence
<220> FEATURE:
<223> OTHER INFORMATION: Primer

<400> SEQUENCE: 16
gagaagttgt cgtccacagg ta                                           22

<210> SEQ ID NO 17
<211> LENGTH: 22
<212> TYPE: DNA
<213> ORGANISM: Artificial Sequence
<220> FEATURE:
<223> OTHER INFORMATION: Primer

<400> SEQUENCE: 17
gcatctgcga gcacgagacg ct                                           22

<210> SEQ ID NO 18
<211> LENGTH: 22
<212> TYPE: DNA
<213> ORGANISM: Artificial Sequence
<220> FEATURE:
<223> OTHER INFORMATION: Primer

<400> SEQUENCE: 18
cgccttggcc ttctcctgct gt                                           22
```